United States Patent
Wong et al.

(10) Patent No.: US 7,392,707 B2
(45) Date of Patent: Jul. 1, 2008

(54) MINIATURE OPTICALLY COUPLED ELECTRICALLY ISOLATED ULTRASENSITIVE DYNAMIC PRESSURE DETECTOR

(75) Inventors: Lid B. Wong, San Diego, CA (US); Hua Mao, San Diego, CA (US); Donovan B. Yeates, Chicago, IL (US); Kim SangKyung, Atlanta, GA (US); Peter Hesketh, Atlanta, GA (US)

(73) Assignee: BioTechPlex Corporation, San Marcos, CA (US)

( * ) Notice: Subject to any disclaimer, the term of this patent is extended or adjusted under 35 U.S.C. 154(b) by 0 days.

(21) Appl. No.: 10/546,966

(22) PCT Filed: Feb. 19, 2004

(86) PCT No.: PCT/US2004/004942

§ 371 (c)(1),
(2), (4) Date: Apr. 11, 2006

(87) PCT Pub. No.: WO2004/075717

PCT Pub. Date: Sep. 10, 2004

(65) Prior Publication Data

US 2006/0225510 A1      Oct. 12, 2006

Related U.S. Application Data

(60) Provisional application No. 60/449,721, filed on Feb. 24, 2004.

(51) Int. Cl.
  *G01L 7/08* (2006.01)
(52) U.S. Cl. .................................................. 73/715
(58) Field of Classification Search .................. 73/715, 73/700
  See application file for complete search history.

(56) References Cited

U.S. PATENT DOCUMENTS

| 4,703,757 A | 11/1987 | Cohen |
| 5,142,155 A | 8/1992 | Mauze et al. |
| 6,238,339 B1 | 5/2001 | Fiddian-Greene et al. |
| 6,272,370 B1 | 8/2001 | Gillies et al. |
| 6,537,232 B1 | 3/2003 | Kucharczyk et al. |
| 6,820,487 B2 * | 11/2004 | Esashi et al. ..................... 73/5 |
| 2002/0162399 A1 * | 11/2002 | Esashi et al. .................. 73/715 |

* cited by examiner

*Primary Examiner*—Andre J Allen
(74) *Attorney, Agent, or Firm*—Wood Phillips Katz Clark & Mortimer

(57) ABSTRACT

A system for monitoring low dynamic pressures in confined spaces, such system comprising a catheter, a multilayered corrugated membrane of diameter less than 2 mm with a reflective inner layer mounted within said catheter; a set of optical fibers comprising one or more illuminating fibers and two or more detecting fibers which are contained within said catheter and whose ends are set at differing distances from the membrane; an illuminating system coupled to said illuminating fibers; and a detection system coupled to said illuminating fibers.

10 Claims, 6 Drawing Sheets

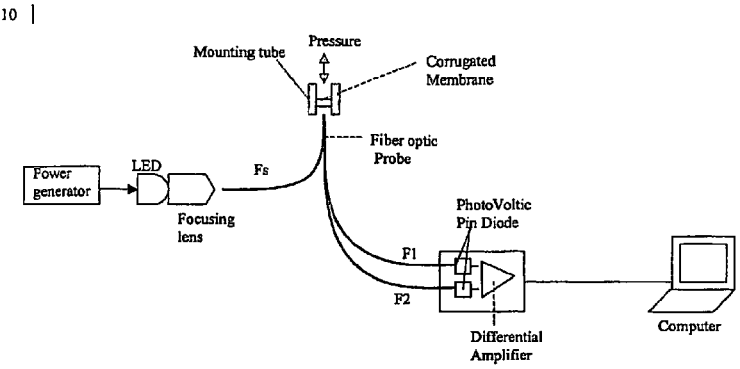
Fig1. Schematics of the fiber-optic linked pressure sensing system (FOLPS)

a.
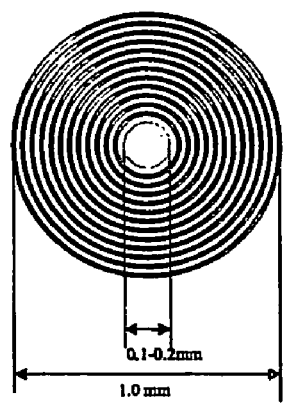
b.
Fig2. Dimension of the corrugated membrane, and one example of the fabricated membranes.

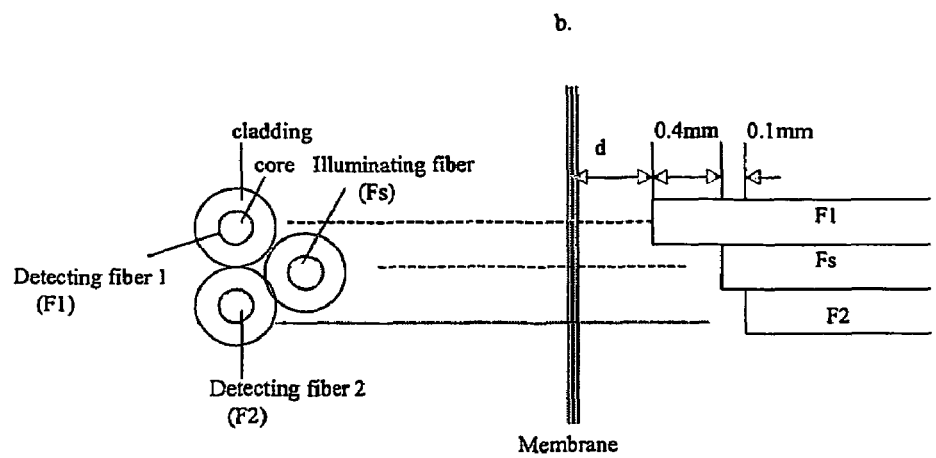
Fig 3 Configuration of the fiber optic bundle and the position of each of its fibers in relation to the corrugated membrane Fig 4
a.
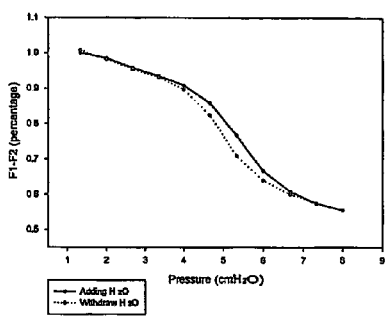
b.
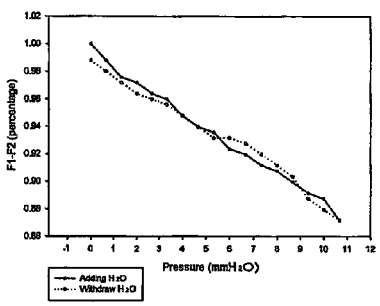
Fig 4a: Dynamic rang
Fig 4b: Resolution of
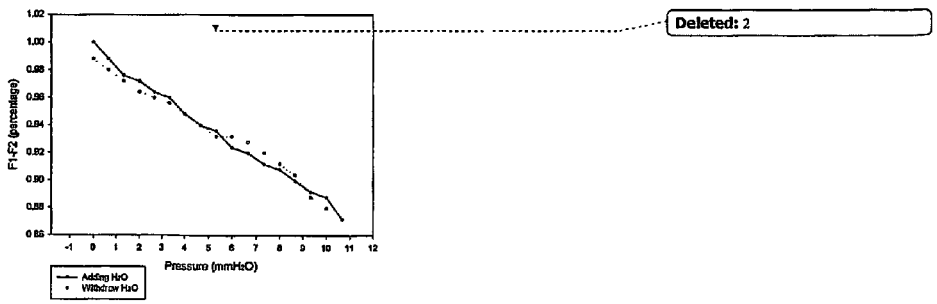

Fig 5
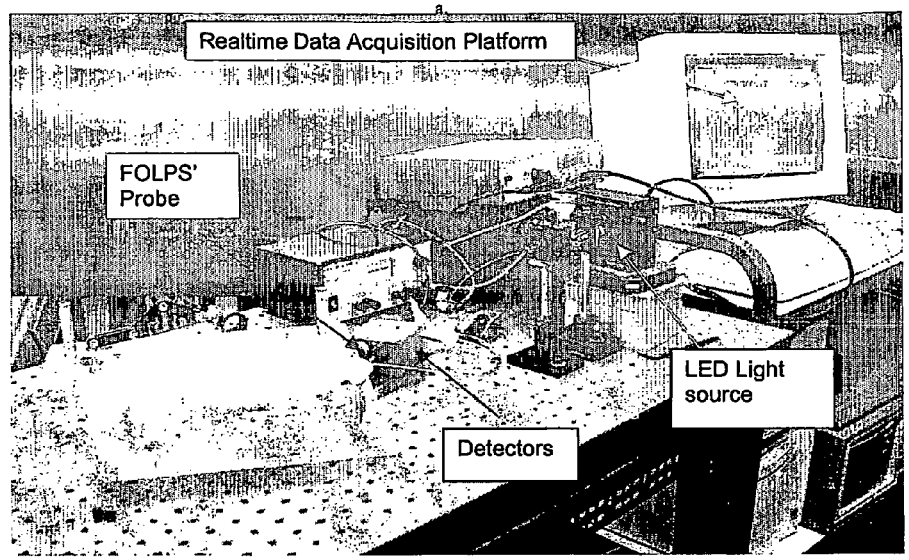
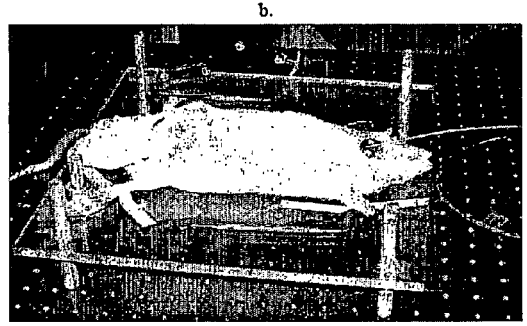
Fig 5a: Experimental setup of the fiber-optic-linked pressure sensor for measuring rat tracheal pressure. Fig 5b: Measurement of rat tracheal pressure following tracheotomy.

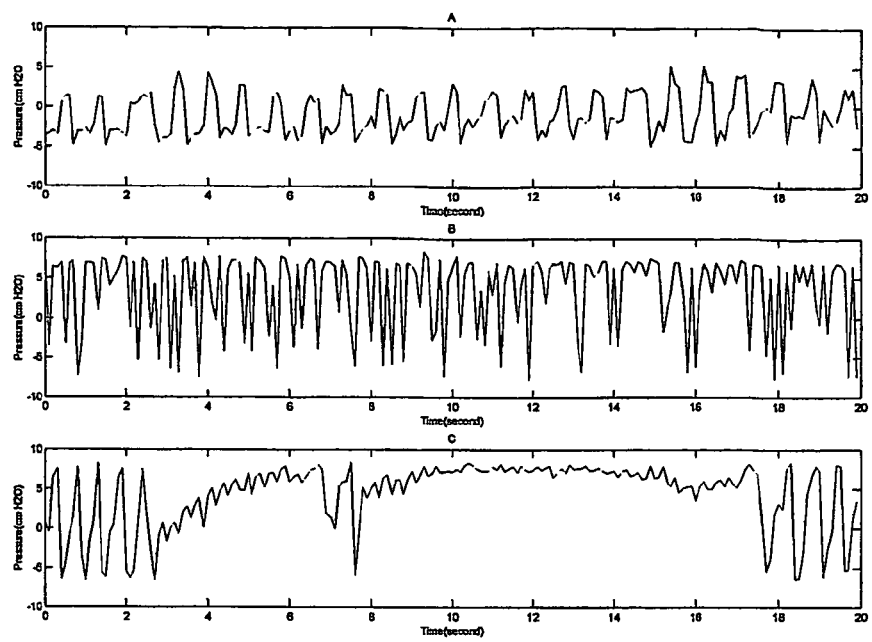
Fig 6: Upper Panel: Baseline airway pressure tracing. Middle Panel: Period doubling breathing occurred at ~ 2min following injection of Neostigmine. Lower Panel: Apnea induced by Neostigmine, ~5 minute following injection.

MINIATURE OPTICALLY COUPLED ELECTRICALLY ISOLATED ULTRASENSITIVE DYNAMIC PRESSURE DETECTOR

CROSS REFERENCE TO RELATED APPLICATION

This application is a Section 371 application of International Application No. PCT/US04/04942, filed Feb. 19, 2004 which claims the benefit of U.S. Provisional Application 60/449,721, filed on Feb. 24, 2004.

GOVERNMENT SUPPORT

The present invention was made with U.S. Government support from the National Center for Research Resources, National Institutes of Health, under Grant No. RR 15150. The U.S. Government has certain rights in this invention.

FIELD OF THE INVENTION

This invention relates generally to diagnostic systems, and in particular to the measurement of physiological function in living animals.

BACKGROUND OF THE INVENTION

Pressure measurements are central to monitoring the status of many physiological functions and, thus, to the monitoring of the progress of many diseases. Such pressure measurements as arterial and venous blood pressures, intra-cranial fluid pressure, or transpulmonary airway pressure all use devices that measure pressures in a range greater than 4 cm $H_2O$. Such devices typically use narrow bore tubing to transduce the pressure from the region of interest to the pressure sensor outside the body, or use fiber-optics to transmit and receive light reflected from a pressure-sensitive device such as a diaphragm located at the tip. The use of narrow bore tubing introduces multiple artifacts into the measurements, especially when the frequency of the measured signal is high and when the volume of the "cavity" where the pressure to be determined is low. Current fiber-optics based systems, utilizing either a single detecting fiber or a bundle of fibers whose detecting tips are set at a single fixed distance from the displacement diaphragm, are not sensitive enough to detect the small (less than 2 cm $H_2O$) rapidly changing pressures that are the goal of this invention. No system or method is currently available that can reliably measure artifact-free dynamic pressures in the range less than 10 cm $H_2O$ with high resolution in small confined body spaces, as for example, those of the dimensions of the rat trachea. For detailed analysis of, e.g., pulmonary function in small animals, it is necessary to monitor pressures in the range 0-10 cm $H_2O$, with a resolution of 0.1 mm $H_2O$. For such small laboratory animals as the rat, the diameter of the probe must be less than 3 mm. The system must also be electrically isolated and immune from environmental electrical and magnetic interference, have a large signal-to-noise ratio, and a wide dynamic range suitable for both normal and pathological conditions.

Accordingly, there is a need for an improved system and method for dynamically monitoring ultra-low pressures in the range 0-10 cm $H_2O$, with a resolution of 0.1 mm $H_2O$ in confined spaces less than 3 mm in diameter. The present invention meets all these criteria.

BRIEF DESCRIPTION OF THE DRAWINGS

FIG. 1 is a drawing of the fiber-optic linked pressure sensing system, according to the present invention.

FIG. 2 is an example of a fabricated ultra-small corrugated membrane, containing a central reflecting surface, according to the present invention. FIG. 2a is a drawing of the membrane, with dimensions noted, of the membrane in the photograph 3b.

FIG. 3a is a drawing of the fiber-optic bundle, according to the present invention.

FIG. 3b is a drawing of the positions of the tips of the fibers relative to the corrugated membrane, according to the present invention.

FIGS. 4a and 4b are graphs of the sensitivity of the device, in terms of percentage membrane deflection versus pressure, in mm $H_2O$.

FIGS. 5a and 5b are photographs of the method of the present invention, in use measuring the tracheal pressure in a laboratory rat.

FIG. 6 is a graph of dynamic pressure obtained in the experiment shown in FIG. 5.

The accompanying drawings, which are incorporated in and form a part of this specification, illustrate embodiments of the invention and, together with descriptions, serve to explain the principles of the invention. They are not intended to limit the scope of the invention to the embodiments described. It is appreciated that various changes and modifications can be made without departing from the spirit and scope of the invention as defined in the appended claims.

SUMMARY OF THE INVENTION

The present invention relates to a system and method for measuring dynamic pressure in the confined space of a small laboratory animal such as a rat, in the range 0-10 cm $H_2O$, with a resolution of 0.1 mm $H_2O$. The system advances the state of the art by providing higher sensitivity and greater range than present systems. A preferred embodiment of the system utilizes three optical fibers, one illuminating fiber and two detecting fibers set at different fixed distances from the corrugated polymer membrane, which are contained within a catheter upon which a corrugated polymer membrane is mounted. The membrane has a diameter of 1.0 mm, a thickness of 1 μm, and a reflective center with a diameter in the range 100-200 μm. The illuminating fiber is coupled to a light emitting diode (LED) light source with a fiber-optics coupling lens. The detecting fibers are coupled to PIN (Positive-Intrinsic-Negative) photodiodes connected to a differential amplifier to reliably determine the difference in the light signals from the two detecting fibers. The output from the differential amplifier is sent to a computer for processing and display.

DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. The invention is intended to cover alternatives, modification, and equivalents which may be included within the invention as defined by the appended claims.

FIG. 1 is a drawing of the fiber-optic linked pressure sensing system. In the preferred embodiment, three optical fibers constructed of conventional materials are contained within a catheter with an outside diameter of 1.5 mm A corrugated polymer membrane, 1 mm in diameter, is mounted on the probe end of the tube. One of the optical fibers, the illuminating fiber, is coupled to a light-emitting diode (LED) system through a fiber-optic coupling lens. The other two fibers, the detecting fibers, are each coupled to a PIN photodiode diode. The two PIN diodes are connected to a differential amplifier with high common mode rejection ratio, whose output is sent to a display system.

FIG. 2 is a drawing of the corrugated membrane that is mounted on the end of the catheter. In a preferred configuration, the membrane is 1 mm in diameter, 1 µm thick, has a 5 µm corrugation height, and a 30 µm corrugation period. It also has a reflective center in the range 100-200 µm in diameter and a pressure range of 0 to 10 cm $H_2O$ with a resolution of 0.1 mm $H_2O$. The exposed surfaces of the corrugated membrane comprise any suitable polymer, as for example, a spin-coatable polymer such as parylene. In a preferred configuration, it is a three-layer membrane, composed of parylene-platinum-parylene, to give a shining surface only at the very flat center of the membrane, to optimize the reflection properties of the membrane for optical measurements. The parylene-platinum-parylene membrane is fabricated using the following microelectromechanical system (MEMS) fabrication protocol. A clean 3" silicon substrate is used. Positive photo-resist of 5 µm thickness is deposited as substrate by spin-coating (Shipley$_{1818}$) at 500 rpm for 45 seconds, then at 4000 rpm for 5 seconds. Hardening is accomplished by baking the sample for 5 minutes at 90° C. A chrome corrugated membrane mask is then overlaid on the top of the photoresist The pattern is generated by exposing the substrate to 405 nm UV irradiation for 18 seconds at 20 mW. The membrane pattern is developed by agitation in 20% Shipley$_{351}$. A 0.5 µm parylene film is deposited again on the top of the photoresist. A 0.1 µm platinum film is deposited on the top of the parylene. A second layer of 0.5 µm parylene is then deposited. The membrane is released by 3-4 hrs slow agitation in acetone. An example of such a fabricated corrugated membrane is shown in FIG. 2.

FIG. 3a is a drawing of the three fibers in the fiber-optic bundle. In the preferred configuration, the fibers have a core diameter of 200 microns, and a low refractive-index cladding 225 microns thick.

FIG. 3b shows a preferred arrangement of the fibers that yields an optimal signal to noise ratio. They are arranged so that the end of the illuminating fiber is 800-900 microns from the corrugated membrane, while the two detecting fibers are, respectively, 400 microns and 1000 microns from the corrugated membrane. The displacement of the reflecting membrane is derived from the differences between the light signals received by the two detecting fibers.

FIG. 4 is an example of an experiment in which the catheter tip measured the pressure of water of varying depth. FIGS. 4a and 4b show the sensitivity of the sensor over different ranges of pressure. FIG. 4a shows the sensitivity in percent change over the range 1-8 cm $H_2O$. FIG. 4b shows the sensitivity in percent change over the range 1-11 mm $H_2O$. The normalized signal from the differential analyzer is plotted against the depth of the water when pressure is increased (adding water) or decreased (withdrawing water). From FIG. 4b, the average sensitivity of the device was 1.2% change per 1 mm $H_2O$ pressure change for both increasing and decreasing pressures.

FIG. 5a is a photograph of an experiment utilizing the present invention. A rat was anesthetized using IM ketamine (44 mg/kg) and intubated with an endotracheal tube. The fiber-optics probe was advanced through the endotracheal tube into the lumen of the trachea. The light source was a 590 mn LED with its luminosity adjusted to a level consistent with the dynamic range of the PIN detector. Baseline pressures were recorded first. Neostigmine, an anti-cholinesterase agent was injected intra-peritoneally and pressures were monitored for several minutes. At the end of the experiment, a tracheotomy was performed to independently determine the tracheal pressure as shown in FIG. 5b.

FIG. 6 contains graphs of the pressure readings obtained in the experiment shown in FIG. 5 and described above. At baseline, the anesthetized rat breathed at 120 breaths/min. Two minutes following injection of neostigmine, the rat exhibited a period doubling breathing pattern. Approximately 5 minutes later, apnea was induced and the rat's breathing gradually returned to normal.

The system and method of the present invention finds particular application for the physiological monitoring of pressure in small laboratory animals. In particular, it is useful for detailed monitoring of intrapulmonary pressure such as the respiratory rate, inspiratory time, expiratory time, tidal volume and peak inspiratory pressure and how they may change in response to environmental insults, drugs, or pathological conditions.

The system and method of the present invention provides a new tool for studying the physiological response of laboratory animals and could find application in clinical monitoring of patients as well.

It can therefore be appreciated that a new and novel system and method for dynamically monitoring ultra-low pressures with high resolution in confined spaces has been presented. It will be appreciated by those skilled in the art that, given the teaching herein, numerous alternatives and equivalents will be seen to exist which incorporate the disclosed invention. As a result, the invention is not to be limited to the foregoing embodiments, but only to the appended claims.

The invention claimed is:

1. A system for monitoring low dynamic pressures in confined spaces, such system comprising:
   a catheter;
   a multilayered corrugated membrane of diameter less than 2 mm with a reflective inner layer mounted within said catheter;
   a set of optical fibers comprising one or more illuminating fibers and two or more detecting fibers which are contained within said catheter and whose ends are set at differing distances from the membrane;
   an illuminating system coupled to said illuminating fibers; and
   a detection system coupled to said illuminating fibers.

2. The system of claim 1, in which the corrugated membrane comprises a minimum of 30 corrugation periods with the corrugation depth not more than 5 µm.

3. The method of claim 1, in which the corrugated membrane has a pressure range 0 to 10 cm $H_2O$ with a resolution of 0.1 mm $H_2O$.

4. The system of claim 1, in which the exposed surfaces of the corrugated membrane is comprised of polymer.

5. The system of claim 1, in which the corrugated membranes has three layers.

6. The system of claim 5, in which the middle layer of the corrugated membrane is comprised of material with good reflective optical properties at visible wavelengths of light.

7. The system of claim 1, in which the illuminating system comprises one or more light emitting diodes.

8. The system of claim 1, in which the detection system comprises one or more PIN diodes.

9. The system of claim 1, in which the detection system comprises a high gain linear differential amplifier with high common mode rejection ratio.

10. The method of claim 1, in which the system is free from magnetic and electrical interference from the region of measurement.

* * * * *